(12) United States Patent
Juttu et al.

(10) Patent No.: US 7,186,872 B2
(45) Date of Patent: Mar. 6, 2007

(54) CATALYST FOR AROMATIZATION OF ALKANES, PROCESS OF MAKING AND PROCESS OF USING THEREOF

(75) Inventors: Gopalakrishnan G. Juttu, Sugar Land, TX (US); Robert Scott Smith, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 10/792,319

(22) Filed: Mar. 3, 2004

(65) Prior Publication Data

US 2005/0197515 A1  Sep. 8, 2005

(51) Int. Cl.
*C07C 2/76* (2006.01)
(52) U.S. Cl. .................................. 585/419; 585/418
(58) Field of Classification Search .............. 585/419, 585/418
See application file for complete search history.

(56) References Cited

U.S. PATENT DOCUMENTS

| | | | |
|---|---|---|---|
| 3,329,480 A | 7/1967 | Young | |
| 3,329,481 A | 7/1967 | Young | |
| 4,180,689 A | 12/1979 | Davies et al. | |
| 4,208,305 A | 6/1980 | Kouwenhoven et al. | |
| 4,704,494 A | 11/1987 | Inui | |
| 4,713,227 A | 12/1987 | Derouane et al. | |
| 4,766,265 A * | 8/1988 | Desmond et al. ........... | 585/415 |
| 4,851,602 A | 7/1989 | Harandi et al. | |
| 4,891,463 A * | 1/1990 | Chu ........................... | 585/415 |
| 5,149,679 A | 9/1992 | Price et al. | |
| 5,192,728 A | 3/1993 | Dessau et al. | |
| 5,456,822 A | 10/1995 | Marcilly et al. | |
| 5,574,199 A | 11/1996 | Beck et al. | |
| 5,693,215 A | 12/1997 | Zones et al. | |
| 5,932,777 A | 8/1999 | Sughrue, II et al. | |
| 6,160,191 A | 12/2000 | Smith et al. | |

FOREIGN PATENT DOCUMENTS

JP  59121115  7/1984

OTHER PUBLICATIONS

"Zeolite Molecular Sieves", D.W. Breck, p. 322, John Wiley & Sons (1974).
NAS (novel aluminosilicates) as catalysts for the aromatisation of propane, Studies of zinc and gallium modified zeolite-based systems having various extents of XRD crystal crystallinity, C. P. Nicolaides et al., Catalysis Today, vol. 71, p. 429-435 (2002).
"Light alkanes aromatization to BTX over Zn-ZSM-5 catalysts, Enhancements in BTX selectivity by means of a second transition metal ion", Louis M. Lubango et al.

\* cited by examiner

*Primary Examiner*—Thuan Dinh Dang
(74) *Attorney, Agent, or Firm*—Jim Wheelington

(57) ABSTRACT

A catalyst of a gallium zeolite on which platinum (Pt/Ga-ZSM-5) has been deposited may be used for aromatization of alkanes having two to six carbon atoms per molecule, such as ethane, propane, butane, etc., to aromatics, such as benzene, toluene and xylenes (BTX). The gallium zeolite contains gallium and silicon in the framework of the zeolite structure. The zeolite structure may be of MFI, FAU, TON, MFL, VPI, MEL, AEL, AFI, MWW or MOR, but preferably, the zeolite has a MFI structure, more preferably is ZSM-5 MFI zeolite. According to the IUPAC recommendations, an example of the sodium form of the zeolite would be represented as:

$$[Na_x \cdot (H_2O)_z][Ga_x Si_y O_{2y+3x/2}]-MFI$$

where x=0.1–25; y=60–100; and z=0.1–10. Platinum may be deposited on the gallium zeolite by ion exchange or impregnation.

9 Claims, 3 Drawing Sheets

CATALYST FOR AROMATIZATION OF ALKANES, PROCESS OF MAKING AND PROCESS OF USING THEREOF

BACKGROUND OF THE INVENTION

1. Field of the Invention

This invention relates to a catalyst for the aromatization of alkanes to aromatics, specifically a zeolite, preferably a MFI-type structure, most preferably a ZSM-5 MFI zeolite, catalyst for the aromatization of alkanes having two to six carbon atoms per molecule to aromatics, such as benzene, toluene and xylene.

2. Description of the Prior Art

Zeolite is a crystalline hydrated aluminosilicate that may also contain other metals, such as sodium, calcium, barium, and potassium, and that has ion exchange properties (Encarta® World English Dictionary [North American Edition]© & (P) 2001 Microsoft Corporation). A method for preparing a zeolite comprises (a) preparing an aqueous mixture of silicon oxide and sources of oxides of aluminum; and (b) maintaining said aqueous mixture under crystallization conditions until crystals of said zeolite form. Much zeolite research has focused on the synthesis of zeolite frameworks containing elements other than silicon and aluminum.

U.S. Pat. No. 6,160,191 discloses that the term "zeolite" includes not only aluminosilicates but substances in which the aluminum is replaced by gallium, titanium, iron or boron and substances in which silicon is replaced by germanium, tin and phosphorous. U.S. Pat. Nos. 3,329,480 and 3,329,481, both issued to D. A. Young, report the existence of crystalline zirconosilicate and titanosilicate zeolites. A zeolite having chromium in the tetrahedral positions has been described by Yermolenko et al at the Second Oil Union Conference on Zeolites, Leningrad, 1964, pages 171–8 (published 1965). However, D. W. Breck, in Zeolite Molecular Sieves, p. 322, John Wiley & Sons (1974) suggests that the chromium present was not present in a zeolite A structure and furthermore was present as an impurity in insoluble form. The impurity was said to be in the form of a chromium silicate as confirmed by the nature of the water vapor adsorption isotherm.

The zeolite ZSM-5 has been synthesized with many elements other than Al in the framework, including iron. Synthesis of an iron-containing zeolitic structure was reported in Japanese Kokai 59,121,115, published Jul. 13, 1984, which disclosed an aluminosilicate having a faujasite structure and containing coordinated iron. The chemical composition is said to be of the formula $aM_{2/n}O:bFe_2O_3:Al_2O_3:cSiO_2$ where M can be H, alkali metal or alkaline earth metal; the symbol n is the valence of M; $a=1+/-0.3$; c is between 4.6 and 100; and a is less than b and both are less than 7. The crystal lattice parameter $a_o$ is between 24.3 and 24.7 angstroms. Similarly, U.S. Pat. No. 4,208,305 discloses crystalline silicates which are structurally a three-dimensional network of $SiO_4^{2-}$, $FeO_4^{2-}$ and, optionally, $AlO_4^-$, $GaO_4^-$ and $GeO_4^-$ tetrahedrons, which are interlinked by common oxygen atoms and are of the overall composition in dehydrated form:

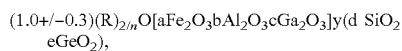

where R is a cation; $a \geq 0.1$; $b \geq 0$; $c \geq 0$; $a+b+c=1$; $y \geq 10$; $d \geq 0.1$; $e \geq 0$; $d+e=1$; and n is the valence of R. Silicates not containing gallium, germanium and aluminum are preferred. Silicates of a particular X-ray powder diffraction pattern are also preferred.

U.S. Pat. No. 4,713,227 discloses crystalline metalloaluminophosphates having microposity, catalytic activity and ion-exchange properties which contain metals such as arsenic, bismuth, cobalt, iron, germanium, manganese, vanadium and antimony within the framework.

U.S. Pat. No. 4,704,494 discloses a process for conversion of low molecular paraffin hydrocarbons to aromatic hydrocarbons using a platinum- or gallium-modified metallosilicate (Si/Me) catalyst where Me is aluminum, gallium, titanium, zirconium, germanium, lanthanum, manganese, chromium, scandium, vanadium, iron, tungsten, molybdenum, nickel or a mixture thereof.

U.S. Pat. No. 5,456,822 discloses a process for aromatization of hydrocarbons containing two to nine carbon atoms per molecule with a catalyst containing an MFI zeolite having silicon, aluminum and/or gallium in the framework, a matrix, and gallium, a noble metal of the platinum family and a metal selected from tin, germanium, indium, copper, iron, molybdenum, gallium, thallium, gold, silver, ruthenium, chromium, tungsten and lead deposited on the zeolite.

U.S. Pat. No. 4,180,689 discloses a zeolite composition for producing aromatic hydrocarbons from aliphatic hydrocarbon feedstock. The zeolite contains gallium which has been exchanged for a cation or proton or impregnated into the zeolitic cavities. This patent teaches that improved yields of aromatic hydrocarbons are realized over zeolites which contain gallium in the form of its oxide substituted either partially or wholly for the aluminum oxide and being part of the crystal structure or the zeolite. There is no disclosure of deposit of platinum on the zeolite.

U.S. Pat. No. 4,851,602 discloses an oligomerization catalyst for conversion of alkanes and alkenes to high octane gasoline with medium pore (about 5–7 angstroms) shape selective crystalline aluminosilicate zeolites. Representative of the shape selective zeolites are ZSM-5, ZSM-11, ZSM-12, ZSM-22, ZSM-23, ZSM-35, ZSM-38, and ZSM-48. The zeolites may be ion exchanged or impregnated with one or more suitable metals, such as Ga, Pd, Zn, Ni, Co and/or other metals of Periodic Groups III to VIII and may include other components, generally one or more metals of group IV, IIB, IIIB, VA VIA or VIIIA of the Periodic Table (IUPAC) such as platinum and other noble metals, such as palladium, gold, silver, rhenium or rhodium. There is no disclosure of gallium as part of the zeolite crystal structure.

U.S. Pat. No. 5,149,679 discloses an intimate mechanical mixture (e.g., ballmilling) of a suitable zeolite (ZSM-5, ZSM-11 or ZSM-12) with a suitable gallium-containing compound to form a gallium containing zeolite catalyst with gallium loadings as low as 2 wt % useful in aromatization of light paraffins. Noble metals such as rhenium, rhodium, nickel, palladium, platinum and iridium may be present in the catalyst but are not necessary. There is no disclosure of gallium as part of the zeolite crystal structure.

U.S. Pat. No. 5,192,728 discloses tin containing microporous crystalline materials which have the same structure as zeolites, such as ZSM-5, and can contain other elements such as boron, iron, chromium and gallium (0–10 wt %). The catalyst may also include a hydrogenation/dehydrogenation metal such as platinum. A Pt/Ga-ZSM-5 catalyst disclosed in comparative data for hexane and heptane aromatization was reported to produce aromatics in low yields and to form $C_3$ and $C_4$ products by cracking.

U.S. Pat. No. 5,574,199 discloses a process for shape selective aromatization of low molecular weight olefins and paraffins to para-xylene with catalytic molecular sieves, such as intermediate pore zeolites, for example, ZSM-5, ZSM-11, ZSM-5/ZSM-11 intermediate, ZSM-12, ZSM-22, ZSM-23, ZSM-35, ZSM-48, ZSM-50, and ZSM-57 with ZSM-5 being preferred, which may be modified with a hydrogenation/dehydrogenation metal selected from Groups IB to VIII of the Periodic Table, including platinum, palladium, nickel, copper, cobalt, gallium, molybdenum, rhodium, ruthenium, silver, gold, mercury, osmium, iron, zinc, cadmium, and mixtures thereof with gallium, zinc and platinum being preferred and gallium being most preferred. The catalyst must have been at least twice contacted with a silicon-containing selectivating agent and calcined prior to the aromatization process.

U.S. Pat. No. 5,932,777 discloses a multi-step reaction/separation process for converting hydrocarbons to aromatics with a catalyst of a zeolite, such as ZSM-5, ZSM-8, ZSM-11, ZSM-12, ZSM-35, ZSM-38, and combinations thereof, which may contain a promoter such as boron, phosphorus, sulfur, gallium, indium, zinc, chromium, silicon, germanium, tin, lead, lanthanides (including lanthanum) or combinations of thereof, which is preferably impregnated on the zeolite. There is no disclosure of gallium as part of the zeolite crystal structure.

U.S. Pat. No. 5,693,215 discloses crystalline borosilicate molecular sieves, i.e., "low-aluminum boron beta zeolite, in which the boron in the crystalline network may be replaced, at least partially, by aluminum, gallium or iron. Hydrogenating components, such as tungsten, vanadium, molybdenum, rhenium, nickel, cobalt, chromium, manganese, or a noble metal, such as palladium or platinum, may be present in the catalyst which is useful in catalytic cracking, hydrocracking and olefin/aromatic formation reactions.

The article "NAS (novel aluminosilicates) as catalysts for the aromatisation of propane, Studies of zinc and gallium modified zeolite-based systems having various extents of XRD crystallinity", C. P. Nicolaides, N. P. Sincadu, M. S. Scurrell, Catalysis Today, volume 71, pages 429–435 (2002), indicates that conversion and BTX selectivity of PtGa-ZSM-5 catalysts are lower than for platinum free Ga-ZSM-5 catalysts and that Ga-ZSM-5 have similar propane conversion but higher BTX selectivity than for H-ZSM-5 catalysts.

The article "Light alkanes aromatization to BTX over Zn-ZSM-5 catalysts, Enhancements in BTX selectivity by means of a second transition metal ion", Louis M. Lubango, Mike S. Scurrell, Applied Catalysis A: General, volume 235 pages 265–272 (2002) refers to platinum-containing catalysts, such as PtGa-ZSM-5, as exhibiting hydrogenolysis resulting in the formation of lower alkanes, e.g., ethane and methane from propane, during aromatization.

It would be advantageous to have a zeolite-type catalyst which has good selectivity for conversion of lower alkanes to aromatics, such as benzene, toluene and xylene, and a high content of ethane in the fuel gas byproduct.

SUMMARY OF THE INVENTION

It has been found that a gallium zeolite on which platinum has been deposited provides a catalyst having good selectivity for conversion of lower alkanes to aromatics. The catalyst is synthesized by preparing a zeolite containing gallium and silicon in the framework, depositing platinum on the zeolite and calcining the zeolite. The gallium zeolite is essentially aluminum-free, e.g., no more than 500 ppm aluminum. The zeolite structure may be of MFI, FAU, TON, MFL, VPI, MEL, AEL, AFI, MWW or MOR, but preferably, the zeolite has a MFI structure, more preferably is ZSM-5 MFI zeolite.

According to the IUPAC recommendations, an example of the sodium form of the zeolite would be represented as:

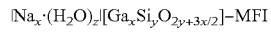

where x=0.1–25; y=60–100; and z=0.1–10.

The catalyst may be used in a process for aromatization of alkanes by contacting the gallium-silicon zeolite on which platinum has been deposited with at least one alkane at aromatization conditions and recovering the aromatic product.

BRIEF DESCRIPTION OF THE DRAWINGS

A more complete appreciation of the invention and many of the attendant advantages thereof will be readily understood by reference to the following detailed description when considered in connection with the accompanying drawings.

DETAILED DESCRIPTION OF THE INVENTION

Figure 1:
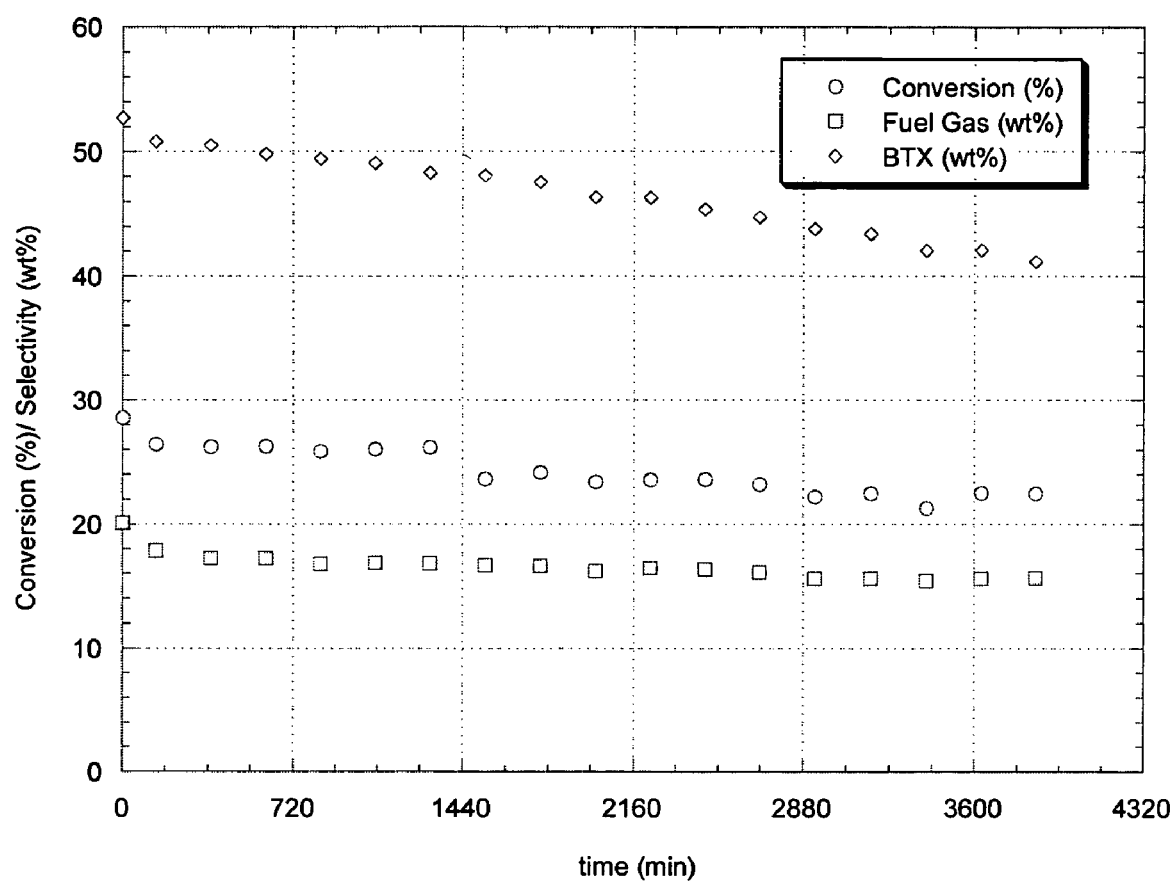
FIG. 1: Run data for the catalyst of Example 1 (per cent conversion of propane, weight per cent of fuel gas and of benzene, toluene and xylene (BTX) in the hydrocarbon product).

Depositing platinum on a MFI zeolite catalyst precursor in which gallium and silicon form the framework of the zeolite has been found to produce a catalyst that has good selectivity for conversion of lower alkanes to aromatics, e.g., alkanes having two to six carbon atoms per molecule to benzene, toluene and xylene.

The zeolite can be prepared by any known method of preparing a MFI structure of gallium and silicon. Zeolites are known to be crystallized silicates and include structures of $TO_4$ tetrahedra, which form a three dimensional network by sharing oxygen atoms where T represents tetravalent silicon and trivalent elements such as aluminum or gallium and, more rarely, boron or beryllium.

Zeolites generally crystallize from an aqueous solution. The typical technique for synthesizing zeolites comprises converting an amorphous gel to zeolite crystals by a hydrothermal process, employing a dissolution/recrystallization mechanism. The reaction medium also contains structure directing agents which are incorporated in the microporous space of the zeolite network during crystallization, thus controlling the construction of the network and assisting to stabilize the structure through the interactions with the zeolite components.

Methods of preparation of a MFI zeolite can be found in U.S. Pat. No. 3,702,886 and in J. Phys. Chem. vol. 97, p. 5678–5684 (1993), hereby incorporated by reference.

The zeolite is essentially aluminum-free, e.g., no more than 500 ppm aluminum. The silicon to gallium atomic ratio (Si:Ga) of the MFI zeolite is preferably greater than 5; more preferably in the range from 5–400, and most preferably in the range from 25–250.

Platinum is deposited on the MFI zeolite by any known method of depositing a metal on a zeolite. Typical methods of depositing a metal on zeolite are ion exchange and impregnation.

One purpose of calcination of the catalyst precursor is to obtain an oxide of the metal components. Calcination also removes volative impurities, including moisture. Calcination may also cause reactions among the elements and compounds present in the catalyst precursor. The catalyst precursor may be calcined at a temperature of 200–600° C. for 1–12 hours. Calcination may be in one stage or multiple stages. Calcination may be done in a high temperature oven or kiln. One example of a calcination would be to begin at room temperature, increase the temperature at a low ramp, e.g, 2–3° C./min, to 250–350° C., hold for 2–5 hours, increase the temperature at a low ramp, e.g., 2–3° C./min, to 450–600° C., hold for 5–8 hours and cool to room temperature.

The catalyst may be supported or bound by oxides of magnesium, aluminum, titanium, zirconium, thorium, silicon, boron and mixtures thereof. Preferably, the support is amorphous and is an oxide of aluminum (alumina).

The catalyst preferably has average pore size preferably in the range from 2–200 angstroms, more preferably in the range from 2–100 angstroms and most preferably in the microporous range from 2–20 angstroms.

A zeolite catalyst may be synthesized by
  a) preparing a zeolite having silicon and gallium in the framework;
  b) depositing platinum on the zeolite; and
  c) calcining the zeolite.

The catalyst may subsequently be treated first with hydrogen, second with a sulfur compound; and then again with hydrogen.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

Synthesis of Ga-ZSM-5 (Ga in the Framework)

Solution #1—In a 250 ml plastic beaker, 6.30 g silicic acid (Fisher Scientific) was dissolved in 30 g of 10 wt % NaOH solution.

Solution #2—In a separate 100 ml-glass beaker, 7.36 g of 98% $H_2SO_4$ (Strem Chemicals) was added to 15 g deionized (DI) water. 0.25 g of $Ga_2O_3$ (Strem Chemicals) was added to this mixture and stirred well until dissolved. 1 g of tetra n-propyl ammonium bromide (TPABr) was added and mixed well.

Solution #3—In a separate 100 ml plastic beaker, 2 g of TPABr was dissolved in 40.8 g of saturated brine (25 wt % NaCl).

Solution #2 was slowly added into solution #1, mixed well and made into a homogeneous mixture. Solution #3 was added and stirred at room temperature for 30 minutes. The molar ratio of this gel is shown in Table 1.

TABLE 1

Gel molar composition of Ga—ZSM-5

| | $SiO_2/Ga_2O_3$ | $H_2O/Ga_2O_3$ | $Na_2O/Ga_2O_3$ | $TPA^+/Ga_2O_3$ |
|---|---|---|---|---|
| Ga—ZSM-5 | 203.41 | 3024.71 | 187.14 | 2.81 |

The gel was loaded into a PTFE-lined 300 ml autoclave and placed in an oven at 160° C. for 80 hours without any agitation. The synthesis was stopped by quenching the autoclave in cold tap water. The zeolite was filtered, washed with 500 ml DI water, dried overnight at 90° C. and calcined in a muffle furnace with air flow according to the following temperature program: Room Temp (RT)→2° C./min→350° C. (hold 3 hours)→2° C./min→550° C. (6 hours)→RT. The elemental analysis of the sample is shown in Table 2. The main powder XRD reflections of the Ga-ZSM-5 are listed in Table 3 (Radiation: Cu—K-α(alpha), wavelength: 1.54 angstroms).

TABLE 2

Elemental analysis of Ga—ZSM-5

| | Element | |
|---|---|---|
| | Si | Ga |
| Weight % | 41.72 | 1.14 |

TABLE 3

Powder XRD intensities

| d-spacing (Å) | Relative Intensity |
|---|---|
| 11.19 | 100 |
| 9.98 | 29 |
| 9.77 | 14 |
| 6.37 | 14 |
| 5.99 | 11 |
| 3.86 | 46 |
| 3.82 | 33 |
| 3.76 | 13 |
| 3.72 | 16 |
| 3.65 | 14 |

Binding and Pt Ion Exchange of Ga-ZSM-5 to form Pt/Ga-ZSM-5

12.67 g of the Ga-ZSM-5 zeolite was then bound with 8.91 g HiQ-40 (pseudo bohemite, Alcoa) and calcined at 550° C. The final material has approximately 67 wt % zeolite. The material was crushed and sized to 20–40 mesh. Platinum was then introduced onto the catalyst by mixing 11.3 g of the catalyst with 45 ml 0.05M $Pt(NH_3)_4(NO_3)_2$ solution. The final catalyst has 0.86 wt % Pt metal.

COMPARATIVE EXAMPLE 1

Synthesis of Pt/Ga/ZSM-5 (Gallium Impregnated)

21.44 g of ZSM-5 powder ($SiO_2/Al_2O_3$=55) was bound with 30.63 g of HiQ-40 pseudo-bohemite (Alcoa). After calcination in air at 550° C., the bound catalyst has 50 wt % zeolite content. The catalyst was then ion-exchanged with $NH_4NO_3$ and calcined in air to 550° C. to convert the zeolite into its acid form. Gallium was incipiently impregnated onto the catalyst by adding 7.52 g of 0.85M $Ga(NO_3)_3$ solution to 15.09 g of catalyst. The catalyst was then calcined in a muffle furnace with air flow at 550° C. The amount of Ga on the catalyst was 2.9 wt %. Platinum was deposited onto the Ga/ZSM-5 by incipient wetness. The final loading of platinum on the catalyst was 1.0 wt %.

COMPARATIVE EXAMPLE 2

Synthesis of Pt/ZSM-5

45 g of ZSM-5 ($SiO_2/Al_2O_3$=90) was bound with HiQ-40 (pseudobohrmite, Alcoa), calcined, crushed and sized to approximately 1 mm. The bound zeolite was ion exchanged with $NH_4(NO_3)$ and calcined at 550° C. to obtain the acid form of the zeolite. The bound acid zeolite was ion exchanged with a 0.05 M $Pt(NH_3)_4(NO_3)_2$ solution. The catalyst was then calcined in air at 400° C. The loading of Pt on this catalyst is 1.3 wt %.

Catalytic Test Results

The catalysts of Example 1 (Pt/Ga-ZSM-5) and Comparative Examples 1 and 2 (Pt/Ga/ZSM-5 and Pt/ZSM-5, respectively) were tested under the following conditions:

Reactor pressure 22 psig, WHSV=$1h^{-1}$, and pure propane feed.

The results are summarized in Table 4.

TABLE 4

| | Catalytic data at TOS = 1 day | | | |
|---|---|---|---|---|
| Catalyst | Temperature (° C.) | Conversion (%) | Fuel (wt %) | Gas BTX (wt %) |
| Example 1 | 500 | 27 | 18 | 50 |
| Comparative Example 1 | 445 | 50 | 52 | 28 |
| Comparative Example 2 | 480 | 55 | 45 | 37 |

Selectivities of fuel gas ($C_1$ and $C_2$) and BTX (benzene, toluene and xylenes) are reported as percentage weight of all hydrocarbon products.

Figure 2:
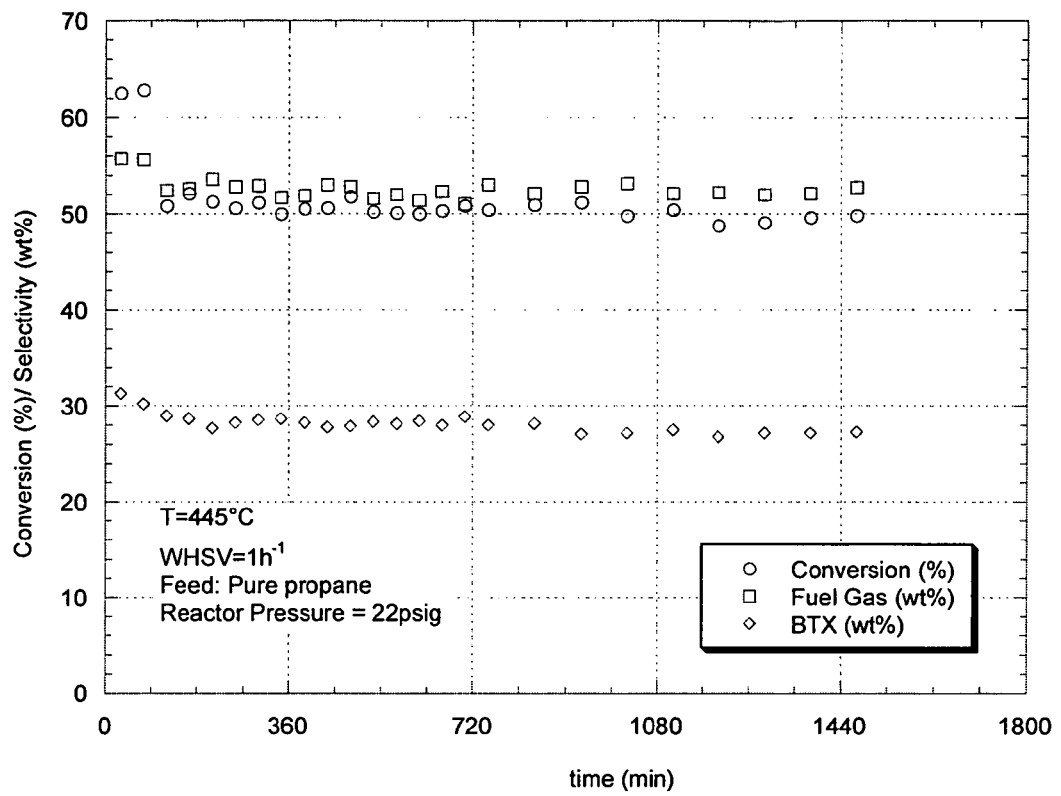
FIG. 2: Run data for the catalyst of Comparative Example 1 (per cent conversion of propane, weight per cent of fuel gas and of benzene, toluene and xylene (BTX) in the hydrocarbon product).
Figure 3:
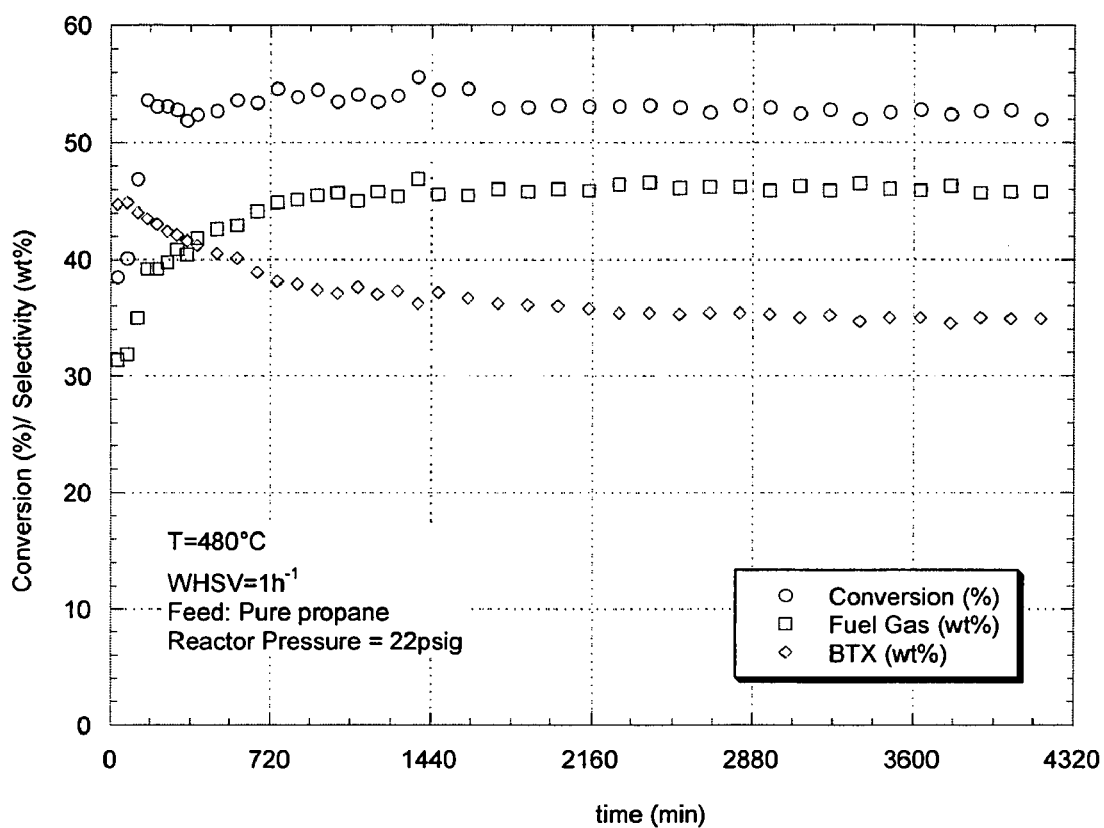
FIG. 3: Run data for the catalyst of Comparative Example 2 (per cent conversion of propane, weight per cent of fuel gas and of benzene, toluene and xylene (BTX) in the hydrocarbon product).

The catalyst of Example 1 (FIG. 1) has stable fuel gas selectivity and conversion and while the BTX selectivity decreases with time on stream (TOS) it remains higher than that for the other catalysts. The catalyst of Comparative Example 1 (FIG. 2) has stable conversion and fuel gas and BTX selectivities and the catalyst of Comparative Example (FIG. 3) has stable conversion but BTX selectivity decreases and fuel gas selectivity increases with time on stream.

What is claimed as new and desired to be secured by Letter of Patent of the United States of America is:

1. A process for the aromatization of hydrocarbons comprising:
    a) contacting an alkane containing 2 to 6 carbon atoms per molecule with a catalyst consisting essentially of platinum on a MFI zeolite consisting essentially of gallium, silicon, and oxygen in the framework and
    wherein the catalyst has been treated first with hydrogen, second with a sulfur compound, and then again with hydrogen; and
    b) recovering an aromatic product.

2. The process of claim 1 wherein the zeolite has a silicon to gallium atomic ratio (Si/Ga) greater than 5.

3. The process of claim 1 wherein the silicon to gallium atomic ratio in the range of from 5–400.

4. The process of claim 3 wherein the silicon to gallium atomic ratio in the range of from 25–250.

5. The process of claim 1 wherein platinum is present at 0.86 wt % of the final catalyst.

6. The process of claim 1 wherein the contact between the alkane and the catalyst is at a space velocity in the range between 0.1 and 100 $h^{-1}$.

7. The process of claim 6 wherein the contact between the alkane and the catalyst is at a temperature in the range between 200 and 600° C.

8. The process of claim 7 wherein the contact between the alkane and the catalyst is at a pressure in the range between 5 and 215 psia.

9. The process of claim 1 wherein the zeolite has a ZSM-5 MFI structure.

* * * * *